Patent …

United States Patent [19]

Braund et al.

[11] 4,346,077

[45] Aug. 24, 1982

[54] METHOD FOR REDUCING INCIDENCE OF PERIPARTURIENT DISORDERS IN COWS

[75] Inventors: Darwin G. Braund, Fayetteville; Thomas J. Fronk, Newfield, both of N.Y.; Richard L. Goings, Nashua; John W. Peters, Manson, both of Iowa; Robert L. Steele, Syracuse, N.Y.

[73] Assignee: Agway, Inc., Syracuse, N.Y.

[21] Appl. No.: 253,374

[22] Filed: Apr. 13, 1981

Related U.S. Application Data

[63] Continuation-in-part of Ser. No. 132,483, Mar. 21, 1980, abandoned.

[51] Int. Cl.³ ...................... A61K 33/06; A61K 33/10
[52] U.S. Cl. ...................................... 424/156; 424/154
[58] Field of Search ................................ 424/156, 154

[56] References Cited

FOREIGN PATENT DOCUMENTS 1542838  3/1979  United Kingdom ................ 424/156

OTHER PUBLICATIONS

Yearbook of Agriculture, "Animal Diseases," U.S.D.A. (1956), p. 244.
Yearbook of Agriculture, "Keeping Livestock Healthy", U.S.D.A. (1942), p. 534.
Milks, Veterinary Pharmacology, Materia Medica & Therapeutics, 6th Ed., (1949), p. 451.
Miller et al., Encyclopedia of Animal Care, 6th Ed., (1962), p. 545.

*Primary Examiner*—Sam Rosen
*Attorney, Agent, or Firm*—Charles S. McGuire

[57] ABSTRACT

The invention comprises an improved method for administering calcium dosages to periparturient dairy cows, resulting in significant decreases in the incidence of milk fever and retained placenta. The single dosage comprises 18 to 36 grams of readily absorbable calcium, preferably finely powdered calcium carbonate in an amount which provides about 30 grams of available calcium. The dosage, preferably in the form of one or more compacted pellets, is administered orally within a period of 0 to 8 hours (preferably 0–2 hours) after parturition. The oral dosage is forcefully administered, as opposed to being offered to the cow in the form of a feed or drinking water supplement.

8 Claims, No Drawings

METHOD FOR REDUCING INCIDENCE OF PERIPARTURIENT DISORDERS IN COWS

This application is a continuation-in-part of Ser. No. 132,483 filed Mar. 21, 1980, and now abandoned.

BACKGROUND OF THE INVENTION

The present invention relates to a nutritional method for reducing the incidence of frequently encountered health problems in periparturient cows and, more specifically, to an improved method for calcium administration in dairy cows.

Parturition and the onset of lactation impose severe physiological stresses on the dairy cow. It has long been recognized that severe hypocalcemia or low blood calcium, which is a common condition of periparturient cows, is a direct cause of milk fever. Also, calcium is very important for muscle contraction and is essential for normal uterine contractions in expelling the placenta.

Intravenous injections of a calcium solution have been used as a treatment for milk fever, after the onset thereof. However, a relatively high time and cost are involved in intravenous administration, as well as creating a new danger of death from the rapid increase thus produced in the blood calcium level. The practice of injecting calcium intravenously as a cure for milk fever is discussed in Yearbook of Agriculture "Keeping Livestock Healthy" U.S. Department of Agriculture, 1942, at page 584. The 1956 edition of the same publication, at page 244, also recognizes the calcium adminstration may be beneficial for cows that have had milk fever, but does not suggest the level of dosage, manner of administration, etc., and concludes that none of the previously attempted methods of preventing milk fever has had much success.

Among the various methods which have been suggested for maintaining or restoring blood-calcium levels to combat milk fever or other calving-related health disorders are those which involve prolonged dietary programs. That is, cows are given special supplements along with their usual rations over a prolonged period which may extend both before and after parturition. An example of this type of this type of dietary plan is that described in British Pat. No. 1,542,838. This method involves maintaining the available calcium intake of the cow at about 30 grams per day for a period of at least 4 to 5 weeks until at least one day prior to parturition, at which time the intake is increased to a level of 50 to 130 grams. Since the exact time of parturition is difficult to judge in advance, this method is subject to errors in estimating the future time of parturition. Furthermore, the method requires special delivery supervision and control over each cow in a herd in accordance with projected calving dates during a period of many weeks which is obviously a tedious and time consuming task, subject to further errors.

A principal object of the present invention is to provide improved methods of establishing blood calcium levels in periparturient dairy cows which significantly reduce health problems connected with hypocalcemia prior to the onset thereof.

Another object is to provide preventive methods of the aforementioned type which are fast, efficacious and easy to administer.

A further object is to provide methods of controlling health disorders prior to the onset thereof in periparturient dairy cows which employ inexpensive and readily accessible materials.

Still another object is to provide a method for significantly reducing the incidence of calving-related health disorders in dairy cows which does not involve estimation of future parturition dates while insuring that each cow receives the necessary dosage in a single step.

Other objects will in part be obvious and will in part appear hereinafter.

SUMMARY OF THE INVENTION

In accordance with the foregoing object, the invention contemplates a preventive method comprising the administration to all cows within a period of 8 hours, and preferably within 2 hours, after parturition of a forced oral dosage of readily absorbable calcium. As used herein, the term "readily absorbable calcium" denotes any calcium source which produces within a period of not more than one hour after ingestion a blood calcuim level which prevents the onset of milk fever. The calcuim is preferably in the form of finely ground or powered calcium carbonate ($CaCO_3$) and is given in a single, forced, oral dosage of about 30 grams. The dosage may be administered in the form of a drench, i.e., in a water solution which is forcibly pumped into the cow's esophagus, or in gelatin capsules, but is preferably contained in a compacted pellet or bolus, one or more of which (forcibly administered together) may constitute a complete dosage. In this (bolus) form the nutritional supplement is convenient to package, store, handle, and administer, and may contain other dietary supplements. A preferred form of bolus contains about 20% by weight insert binder and about 80% active ingredients, 90% to 95% of which is finely ground calcium carbonate.

DETAILED DESCRIPTION

The present invention is based upon and is verified by certain in field tests which were performed on a number of herds of dairy cows. In each of three tests, described separately in the following paragraphs, dry cows on each farm were alternately assigned at the beginning of the trial period to either control or experimental groups based on projected calving date. No first-calf heifers were included. Cooperating dairymen had to have adequate cow identification and individual cow health records. The trial objective and procedures were discussed with the dairyman and his respective herd veterinarian prior to initiation of the trial. This practice was continued throughout the trial. It was requested that the dairyman not alter his "normal" feeding and management practices during the trial.

In one test, cows assigned to the experimental group were offered a mixture of 12 oz. of an experimental supplement in about two gallons of lukewarm water between 30 minutes and 2 hours postpartum. The supplement contained 80% calcium lactate, 16% dried skim milk, 1% sodium bicarbonate, 1% salt and 2% vitamin premix. About 35 grams of calcium was contained in each 12 oz. package. If the supplement could not be offered within the prescribed time, the cow was classified as "missed" and included with the control group in the test results. Control cows received no supplement at any time.

The test included a total of 417 control cows and 466 experimental cows, 121 of which were missed and thus tabulated with the control group. Of the 345 cows offered the experimental supplement, 128 consumed none, 61 about one-quarter, 44 about half, 26 about three-quarters, and 86 all of the water containing the supplement. Post-calving measurements and data were recorded through the first 60 days of lactation.

The incidence of milk fever in the control group was 12.2%. Of the cows consuming less than half the experimental supplement, 10.1% contracted milk fever; of those which consumed one-half or more, the incidence of milk fever was 5.8%. The effect of the supplement on retained placenta was similar, with the control group showing a 20.3% incidence and the experimental groups consuming less than half and more than half of the supplement having incidence rates of 16.9% and 7.1%, respectively. Consumption of at least half the experimental supplement appeared to have similar beneficial effects in lowering the incidence of other health disorders. For example, the control group, those consuming less than and more than half of the supplement averaged 5.8%, 3.7%, and 1.3%, respectively, in incidence of ketosis and 9.3%, 10.6% and 5.1%, respectively, for metritis.

Although the test demonstrated the effectiveness of the oral administration of the nutrient supplement within the prescribed period in a water solution, problems with acceptability in the form offered were encountered. While 62.9% of the cows consumed some portion of the supplement when offered, only 24.9% consumed all of it, and 45.2% consumed at least half. Thus, while oral administration in water solution is effective when consumed, the present invention encompasses only forced oral dosages which, in the case of liquid solutions, would be administered in the form of a drench, a conventional and accepted method of administering forced oral dosages of liquid medicaments.

In another test, the dosage was administered in the form of gelatin capsules filled with an experimental supplement which included 29.5% calcium, 3.11% phosphorus, 4.67% magnesium and fractional percentages of sodium, potassium, copper, iron, manganese and zinc. The experimental supplement was adminstered in a single dosage of three capsules, providing about 31 grams total available calcium, to assigned cows as soon as possible after calving. Time of administration were recorded as less than or more than two hours post-calving. Cows were eliminated from the experimental group if they were not administered the supplement within eight hours after parturition. A group of control cows within each herd tested received no supplement at any time. Post-calving measurements and data were recorded through the first 21 days of lactation.

This test was performed simultaneously at a total of 31 farms and included 322 experimental or test cows and 345 control cows. Of the test cows, 241 received the supplement within 2 hours after calving, and 81 in the period of 2 to 8 hours post-calving. Analysis of data showed significant reduction of retained placenta and milk fever in those animals having single births and receiving the supplement within 2 hours post-calving, actual count being a 54% reduction in the incidence of retained placenta and 55% reduction of milk fever over the control group cows. The experimental supplement appeared to have no effect in cows giving multiple births.

In a third field trial, data were collected from 90 herds, including a total of 1,710 cows. Within herds, dry cows which had milk fever following one or both of the two previous calvings were alternately assigned to the control and experimental groups. Additional dry cows were then assigned in the same manner.

The control cows received a single dosage of a placebo in the form of 3 gelatin capsules filled with solka-floc. The experimental cows received the special nutritional supplement in a single dosage of 3 boluses. The capsules and boluses were administered to assigned cows as soon as possible after calving. The nutritional supplement provided about 30 grams of calcium per administration. Time of administration was recorded as less than or more than 2 hours post-calving. Cows were eliminated from both groups if they were not administered the capsules or boluses within 8 hours post-calving.

The incidence of health problems is based on a total of 848 cows for the control group and 862 cows for the experimental group. A reduction of 65.1% in milk fever incidence between the control and experimental groups was comparable to that observed in the two previously described trials, the milk fever incidence being 6.3% in the control group and 2.2% in the experimental group. In those cows having a previous history of milk fever, those in the control group showed an incidence of 44% vs. 12.5% for the experimental group, a reduction of 71.6%.

The incidence of retained placenta for all cows in the control and experimental group was 21% and 12%, respectively, a reduction of 43% in the cows receiving the supplement. Although the greatest reduction in retained placenta was observed in cows having single births, cases of retained placenta showed a 33.7% reduction in cows having twins. In the two tests previously described, the incidence of retained placenta in cows having twins was similar for the control and experimental groups. This suggests an improvement in efficiency for the supplement in bolus form.

The composition of the boluses administered in this test was 70.12% limestone, 20% inert binder, 6.4% selenium premix and smaller amounts of other nutrients. The limestone was very finely ground, passing through a U.S. 200 mesh screen, and had a calcium content between 36 and 37 percent.

From the foregoing it may be seen that the present invention provides a method for the administration of preventive nutritional supplements which significantly reduces the incidence of milk fever and retained placenta in dairy cows, as well as having apparent beneficial effects on other common calving-related disorders such as ketosis, metritis, displaced abomasum and inappetance. Since the method invloves only a single, forced, oral dosage it is fast, inexpensive, safe and easy to adminster as opposed to prior art methods involving, for example, potentially dangerous injections or supervision and control of diet over a relatively long period of time. Also, the forced dosage is effective over a greater number of cows than prior art methods which depend upon voluntary consumption of the dosage, which often does not occur.

What is claimed is:

1. A nutritional method for reducing the occurrence of milk fever and retained placenta in periparturient cows consisting essentially of administering to each cow a single, forced, oral dosage of nutritional supplement including between about 18 and 36 grams of readily absorbable calcium within a period of 0 to 8 hours after parturition.

2. The method according to claim 1 wherein said readily absorbable calcium is in the form of finely powdered calcium carbonate.

3. The method according to claim 1 wherein said period is 0 to 2 hours after parturition.

4. The method according to claim 2 wherein said period is 0 to 2 hours after parturition.

5. The method according to claims 1, 2 or 3 wherein the amount of readily absorbable calcium in said dosage is about 30 grams.

6. The method according to claims 1, 2 or 3 wherein said dosage is contained in one or more boluses.

7. The method according to claims 1, 2 or 3 wherein the amount of readily absorbable calcium in said dosage is about 30 grams and said dosage is contained in a plurality of boluses which include an inert binder and other active ingredients.

8. The method according to claims 1, 2 or 3 and further including maintaining the normal rations of said cows up to the time of parturition, and thereafter, except for said single dosage.

* * * * *